(12) United States Patent
Del Castillo Nieto et al.

(10) Patent No.: US 8,211,939 B2
(45) Date of Patent: Jul. 3, 2012

(54) ISOSORBIDE NITRATES

(75) Inventors: Juan Carlos Del Castillo Nieto, Barcelona (ES); Marisabel Mourelle Mancini, Barcelona (ES); Francisco Pubill Coy, Cabrils (ES); Lydia Cabeza Llorente, Barcelona (ES); Jose Repolles Moliner, Barcelona (ES)

(73) Assignee: Lacer, S.A., Barcelona (ES)

( * ) Notice: Subject to any disclaimer, the term of this patent is extended or adjusted under 35 U.S.C. 154(b) by 706 days.

(21) Appl. No.: 12/334,986

(22) Filed: Dec. 15, 2008

(65) Prior Publication Data

US 2010/0022638 A1   Jan. 28, 2010

(30) Foreign Application Priority Data

Jul. 22, 2008  (EP) .................................... 08380221

(51) Int. Cl.
*A61K 31/34*   (2006.01)
*C07D 493/04*   (2006.01)
*A61P 9/00*   (2006.01)

(52) U.S. Cl. ....................... 514/470; 549/464
(58) Field of Classification Search ..................... None
See application file for complete search history.

(56) References Cited

U.S. PATENT DOCUMENTS

| | | |
|---|---|---|
| 7,521,571 B2 | 4/2009 | Moliner et al. |
| 7,777,058 B2 | 8/2010 | Moliner et al. |
| 2006/0235052 A1 | 10/2006 | Moliner et al. |
| 2010/0196387 A1 | 8/2010 | Moliner et al. |

OTHER PUBLICATIONS

Moliner et al., caplus an 2005:371266.*

* cited by examiner

*Primary Examiner* — Sun Jae Loewe
(74) *Attorney, Agent, or Firm* — Oblon, Spivak, McClelland, Maier & Neustadt, L.L.P.

(57) ABSTRACT

The present invention relates to new 3-substituted 6-nitrooxy-hexahydrofuro[3,2-b]furane derivatives possessing a superior pharmacological activity in thrombosis and in coronary ischemia models.

5 Claims, No Drawings

ISOSORBIDE NITRATES

FIELD OF THE INVENTION

The present invention relates to new derivatives of isosorbide mononitrate having a potent vasodilating activity and a prolonged duration of action.

BACKGROUND ART

The nitric acid esters of organic compounds, commonly known as nitrated organic compounds, are known and have been used as vasodilating agents for some time. Among these, the usefulness of mono and di-nitrated, isosorbide is well known, and furthermore, compounds with vascular and coronary activities based on substitution reactions on the free hydroxyl group of isosorbide mononitrate have been described. For example, U.S. Pat. No. 4,891,373 patent describes aminepropanol derivatives for the treatment of angina pectoris and systemic and pulmonary hypertension.

U.S. Pat. No. 5,665,766 patent describes isosorbide 5-mononitrate 2-acetylsalicylate as well as its platelets anti-aggregating activity.

One of the main problems of the above-mentioned nitrated organic compounds resides on the fact that these are quite sensitive in relation to the phenomena known as tachyphylaxy or tolerance, which consists in that the organism's response with respect to its effect decreases during prolonged treatment, and it is then required to sensitively and gradually increase the administered doses or otherwise perform a pharmacological wash-out.

It is also known that one way of reducing the tolerance of the nitrated organic compounds consists in introducing thiol groups in the molecule, for example by using sulphur containing amino acids. Thus, European patent EP-B-0362575 describes nitrated organic compounds with incorporated cysteine and, mainly, methionine molecules.

Patent application WO-A-92/04337 describes organic nitrated derivatives of the thiazolidine ring with vasodilating activity and a reduced tolerance.

Patent application WO-A-93/03037 describes an enormous amount of different nitrated organic vasodilating compounds, with reduced tolerance, of highly variable structures.

Patent application WO-A-00/20420 describes isosorbide mononitrates wherein the free hydroxyl group is esterified with either carboxylic acids or with thioacids wherein said ester groups are in trans position with respect to the nitrate group.

Finally, patent application WO-A1-2005/037842 describes isosorbide mononitrates wherein the free hydroxyl group has been replaced by a wide range of substituents.

The compounds described in the art however, are not fully satisfactory as they have a limited duration of action.

It has now been surprisingly found that certain compounds, some of which were claimed but not disclosed in patent application WO-A1-2005/037842, have not only high anti-thrombotic and vasodilatatory activities, but also a longer duration of action than their structural homologues described in said patent application.

SUMMARY OF THE INVENTION

It is an object of the present invention to provide new 3-substituted 6-nitrooxy-hexahydrofuro[3,2-b]furane derivatives having a better pharmacological activity than that of their structural analogues described in the art both in thrombosis models and in coronary vasodilatation models and also displaying a longer duration of action.

A further object of the invention to provide pharmaceutical compositions comprising at least one of said 3-substituted 6-nitrooxy-hexahydrofuro[3,2-b]furane derivatives.

Also, a further object of the present invention is the use of said new 3-substituted 6-nitrooxy-hexahydrofuro[3,2-b] furane derivatives for the preparation of medicaments for the treatment of dysfunctions of the circulatory system such as cardiovascular and coronary dysfunctions.

DETAILED DESCRIPTION OF THE INVENTION

The present invention relates to compounds of formula (I), tautomers, pharmaceutically acceptable salts, prodrugs or solvates thereof:

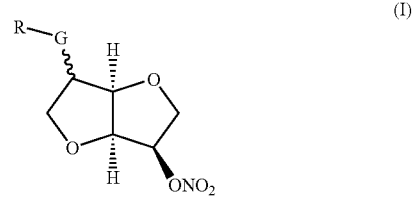

(I)

wherein G represents a —(C=O)—S— group or a —S(O)$_n$— group, being n an integer selected from 0, 1 and 2; and R represents a group selected from $C_1$-$C_3$ alkyl and $C_3$ alkenyl;

with the proviso that when R is a methyl group, the R-G- and —ONO$_2$ groups are in the cis position.

The compounds of formula (I) can be in the form of the cis or trans isomers depending on the relative orientation of the nitrate (—ONO$_2$) and R-G- groups, as it is shown in the following formulae:

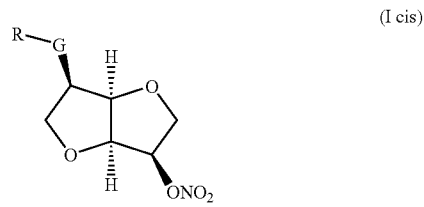

(I cis)

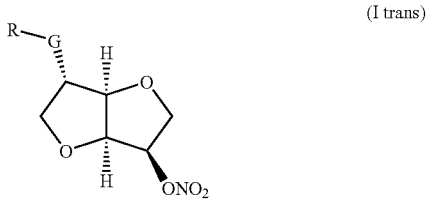

(I trans)

Additionally, when in the compounds of formula (I), G represents a sulfoxide group —(S=O)—, there are four possible diastereomers, as a result of the chiral nature of the sulphur atom in the sulfoxide group.

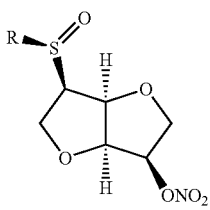
(I cis-a)

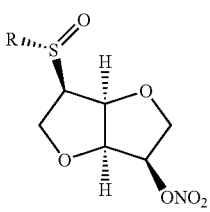
(I cis-b)

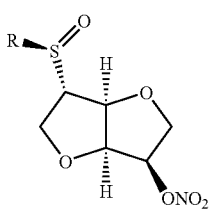
(I trans-a)

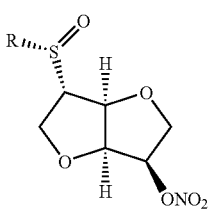
(I trans-b)

An embodiment of the present invention relates to compounds of formula (II), tautomers, pharmaceutically acceptable salts, prodrugs or solvates thereof:

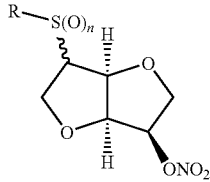
(II)

wherein n is an integer selected from 1 and 2; and

R represents a group selected from $C_2$-$C_3$ alkyl and $C_3$ alkenyl.

Another embodiment of the present invention relates to a compound of formula (III), tautomers, pharmaceutically acceptable salts, prodrugs or solvates thereof

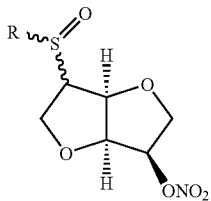
(III)

wherein R represents a group selected from $C_2$-$C_3$ alkyl and $C_3$ alkenyl, more preferably an ethyl, a n-propyl or an allyl group.

Another embodiment of the present invention relates to a compound of formula (VII), tautomers, pharmaceutically acceptable salts, prodrugs or solvates thereof

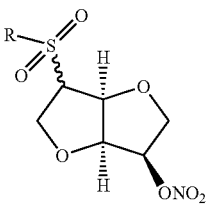
(VII)

wherein R represents a group selected from $C_2$-$C_3$ alkyl and $C_3$ alkenyl, being more preferably an ethyl, a n-propyl or an allyl group.

Still another embodiment of the present invention relates to a compound of formula (IV), tautomers, pharmaceutically acceptable salts, prodrugs or solvates thereof:

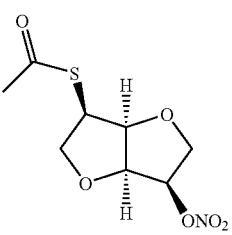
(IV)

Specially preferred are the compounds:
(3R,3aS,6S,6aS)-6-(ethylthio)hexahydrofuro[3,2-b]furan-3-yl nitrate
(3R,3aS,6S,6aS)-6-((S,R)-ethylsulfinyl)hexahydrofuro[3,2-b]furan-3-yl nitrate
(3R,3aS,6S,6aS)-6-((S)-ethylsulfinyl)hexahydrofuro[3,2-b]furan-3-yl nitrate
(3R,3aS,6S,6aS)-6-((R)-ethylsulfinyl)hexahydrofuro[3,2-b]furan-3-yl nitrate
(3R,3aS,6S,6aS)-6-(ethylsulfonyl)hexahydrofuro[3,2-b]furan-3-yl nitrate
(3R,3aS,6S,6aS)-6-(propylthio)hexahydrofuro[3,2-b]furan-3-yl nitrate
(3R,3aS,6S,6aS)-6-((S,R)-propylsulfinyl)hexahydrofuro[3,2-b]furan-3-yl nitrate (3R,3aS,6S,6aS)-6-((S)-propylsulfinyl)hexahydrofuro[3,2-b]furan-3-yl nitrate
(3R,3aS,6S,6aS)-6-((R)-propylsulfinyl)hexahydrofuro[3,2-b]furan-3-yl nitrate
(3R,3aS,6S,6aS)-6-(propylsulfonyl)hexahydrofuro[3,2-b]furan-3-yl nitrate
(3R,3aS,6S,6aS)-6-(allylthio)hexahydrofuro[3,2-b]furan-3-yl nitrate
(3R,3aS,6S,6aS)-6-((S,R)-allylsulfinyl)hexahydrofuro[3,2-b]furan-3-yl nitrate
(3R,3aS,6S,6aS)-6-((S)-allylsulfinyl)hexahydrofuro[3,2-b]furan-3-yl nitrate
(3R,3aS,6S,6aS)-6-((R)-allylsulfinyl)hexahydrofuro[3,2-b]furan-3-yl nitrate
(3R,3aS,6S,6aS)-6-(allylsulfonyl)hexahydrofuro[3,2-b]furan-3-yl nitrate
(3R,3aS,6R,6aS)-6-(ethylthio)hexahydrofuro[3,2-b]furan-3-yl nitrate
(3R,3aS,6R,6aS)-6-((S,R)-ethylsulfinyl)hexahydrofuro[3,2-b]furan-3-yl nitrate
(3R,3aS,6R,6aS)-6-((S)-ethylsulfinyl)hexahydrofuro[3,2-b]furan-3-yl nitrate
(3R,3aS,6R,6aS)-6-((R)-ethylsulfinyl)hexahydrofuro[3,2-b]furan-3-yl nitrate
(3R,3aS,6R,6aS)-6-(ethylsulfonyl)hexahydrofuro[3,2-b]furan-3-yl nitrate
(3R,3aS,6R,6aS)-6-(propylthio)hexahydrofuro[3,2-b]furan-3-yl nitrate
(3R,3aS,6R,6aS)-6-((S,R)-propylsulfinyl)hexahydrofuro[3,2-b]furan-3-yl nitrate
(3R,3aS,6R,6aS)-6-((S)-propylsulfinyl)hexahydrofuro[3,2-b]furan-3-yl nitrate
(3R,3aS,6R,6aS)-6-((R)-propylsulfinyl)hexahydrofuro[3,2-b]furan-3-yl nitrate
(3R,3aS,6R,6aS)-6-(propylsulfonyl)hexahydrofuro[3,2-b]furan-3-yl nitrate
(3R,3aS,6R,6aS)-6-(allylthio)hexahydrofuro[3,2-b]furan-3-yl nitrate
(3R,3aS,6R,6aS)-6-((S,R)-allylsulfinyl)hexahydrofuro[3,2-b]furan-3-yl nitrate
(3R,3aS,6R,6aS)-6-((S)-allylsulfinyl)hexahydrofuro[3,2-b]furan-3-yl nitrate
(3R,3aS,6R,6aS)-6-((R)-allylsulfinyl)hexahydrofuro[3,2-b]furan-3-yl nitrate
(3R,3aS,6R,6aS)-6-(allylsulfonyl)hexahydrofuro[3,2-b]furan-3-yl nitrate
S-(3R,3aS,6R,6aS)-6-(nitrooxy)hexahydrofuro[3,2-b]furan-3-yl ethanethioate
and tautomers, pharmaceutically acceptable salts, prodrugs or solvates thereof.

The compounds of the present invention may be used in therapy for the prevention and/or treatment of atherosclerosis, cardiac allograft vasculopathy, platelet activation, thrombosis, stroke and/or pathological conditions where oxidative stress plays an important role in their pathogenesis such as but not limited to allergy, stroke and Alzheimer's disease and/or ischemic cardiovascular diseases.

The pharmaceutical compositions may be administered by different routes. For example, they may be administered orally in form of pharmaceutical preparations such as tablets, capsules, syrups and suspensions; also, parenterally in form of solutions or emulsions, etc.

They may also be administered topically in form of creams, pomades, balsams, etc., and transdermically for example through the use of patches or bandages. They may also be applied directly in the rectum as suppositories. The preparations may comprise physiologically acceptable carriers, excipients, activators, chelating agents, stabilizers, etc. In case of injections, physiologically acceptable buffers, solubilising agents or isotonics may be added.

The pharmaceutical compositions according to the present invention may further comprise a thrombolytic agent, preferably a plasminogen activator, urokinase, streptokinase, alteplase or anistreplase. They may also contain an anticoagulant agent, preferably heparin, dicoumarol, acenocoumarol, enoxaparine or pentosan polysulfate. Moreover, they may contain additionally an antithrombotic agent preferably acetyl salicylic acid, dipyridamole, ticlopidine, clopidrogel, triflusal, pentosan polysulfate or abciximab. They can further comprise an immunoglobulin or fragment thereof having a specificity for glycoprotein IIb/IIIa.

Alternatively, the pharmaceutical compositions according to the invention may further comprise an hypolipemiant agent preferably simvastatin, lovastatin, atorvastatin, pravastatin, fluvastatin, eptastatin, lifibrol, acifran, acitemate, glunicate or rosuvastatine. They may also contain an antioxidant/free radical scavenging agent, preferably selected from nicaraven, ranolazine, emoxipin, glutatione, edaravone, raxofelast, lycopene, acetylcisteine, N-acetyl-L-cysteine, N-acetyl-D-cysteine, or carvedilol.

The pharmaceutical compositions according to the present invention may be used for the treatment and/or prevention of atherosclerosis, cardiac allograft vasculopathy, platelet activation, thrombosis, stroke, tissue damage due to ischemia and/or due to ischemia-reperfusion, and/or pathological conditions where oxidative stress plays an important role in their pathogenesis (such as but not limited to allergy, stroke, Alzheimer's disease, ischemic cardiovascular diseases); and/or pathological conditions where a deficit of NO (nitrous oxide) plays an important role in their pathogenesis. They can also be used for the treatment and/or prevention of dysfunctions of the circulatory system preferably cardiovascular and coronary dysfunctions.

The daily dose may be varied depending on the specific symptoms, the age, the body weight of the patient, the specific mode of administration, etc., and a daily normal dose for an adult person could vary between 0.1 to 500 mg, and can be administered as a single dose only or divided into several doses during the day.

Another aspect of the present invention relates to the processes for preparing the compounds of formula (I), tautomers, pharmaceutically acceptable salts, prodrugs or solvates thereof.

The compounds of the present invention wherein G represents a thioether group (—S—) may be prepared following a process analogous to the one described in patent application WO2005/037842 by alkylation of the compound of formula (V) (the manufacturing process of which is also described in patent application WO2005/037842) with an alkylating agent of formula R-L wherein R represents a group selected from $C_1$-$C_3$ alkyl and $C_3$ alkenyl and L represents a leaving group such as a bromine atom as it is shown below:

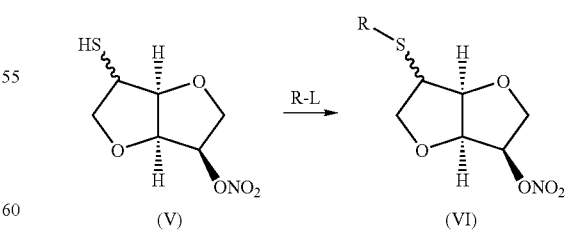

The compounds of the present invention wherein G represents an acylthio group (—COS—) may be prepared using a substitution reaction whereby compounds of formula (VI) wherein $L^2$ represents a leaving group such as a group triflate, tosylate or tetrahydropyranyl are reacted with a compound of formula R—COSK wherein R represents a group selected from $C_1$-$C_3$ alkyl and $C_3$ alkenyl as shown below:

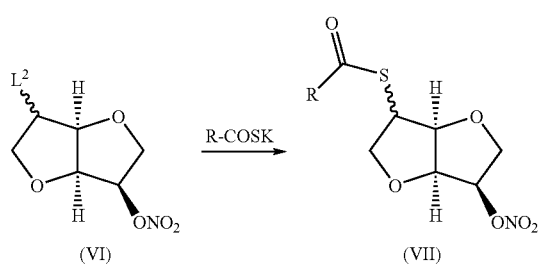

The compounds of the present invention wherein G represents a sulfoxide group (—SO—) may be prepared following a process analogous to the one described in patent application WO2005/037842 by oxidation of a compound of formula (VI) with an oxidising agent as shown below:

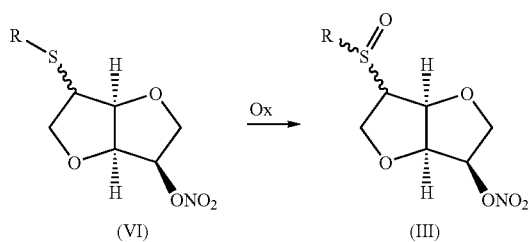

The oxidising agent may be a non-enantiospecific agent such as sodium periodate ($NaIO_4$) when it is desired to obtain a mixture of diastereomers in variable ratio close to 50/50 (within the range 30/70 to 70/30). The separation of stereoisomers may be carried out afterwards by conventional methods such as fractional recrystallization or chromatographic separation. As crystallization solvents the following may be used: acetone, dioxane, chloroform, toluene, isopropanol, . . . etc. This method may be cumbersome, slow and provide low yields.

For these reasons when it is desired to obtain one of the diastereomers it is preferable to carry out an enantioselective oxidation using one of the general methods described in the literature such as:

Cellular cultures
Enzymatic synthesis
Oxidative systems with non-metals (iodinated compounds)
Use of chiral phosphoryl chlorides
Use of oxaziridines
Chiral metallic complexes—catalysed enantioselective oxidations Of all the above mentioned options, it is preferred to use chiral metallic complexes—catalysed enantioselective oxidations. There is plenty of bibliography on asymmetric oxidations catalysed by metallic complexes. The majority of systems are modifications of the Sharpless epoxidation reaction with titanium isopropoxide and diethyltartrate as chiral complexing catalyst using an oxidising agent such as tert-butyl hydroperoxide.

Titanium, manganese, vanadium and iron compounds may be used to form chiral catalysts by the addition of an optically active agent such as for example, (D or L) diethyltartrate, and subsequent addition of the oxidising agent which may or may not be optically active.

Specially preferred are the enantioselective oxidations catalyzed by titanium/L or D diethyl tartrate (I-DET or d-DET) complexes and an oxidising agent such as for example, tert-butyl hydroperoxide or cumene hydroperoxide wherein the molar ratio between the titanium compound (usually titanium isopropoxide), diethyl tartrate and the oxidising agent may be variable (1/1/1; 1/2/1, 2/4/1, etc . . . ). These reactions may be carried out in the presence of water (1 or 2 mol) or under anhydrous conditions.

The compounds of the present invention wherein G represents a sulfone group (—$SO_2$—) may be prepared following a process analogous to the one described in patent application WO2005/037842 by oxidation of a compound of formula (III) with an oxidising agent such as periodic acid ($H_5IO_6$) or sodium periodate as shown below:

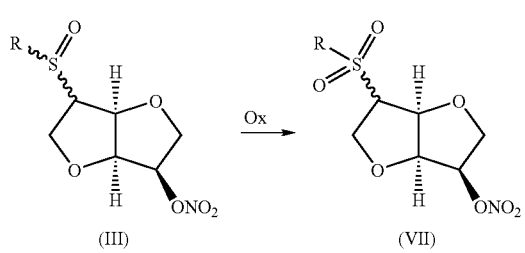

Finally the compounds of the present invention may be prepared by nitration of compounds of formula (VIII) as shown below:

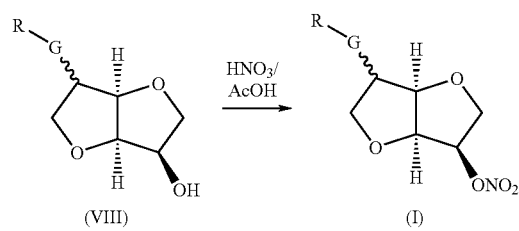

As nitrating agent one may use, for example, a mixture obtained by slow addition at 0° C., of 12 parts by volume of $HNO_3$ (60%) to a mixture of 50 parts by volume of acetic anhydride and 50 parts by volume of acetic acid.

The working examples included in the present specification describe in detail suitable processes to obtain several of the compounds according to general formula (I). In the light of these examples, it is within the general knowledge of the expert in the field to obtain the compounds not explicitly exemplified by suitable modifications of the working examples. It is also obvious for the expert in the field that these examples are only illustrative and should not be taken as a limitation of the scope of the invention.

EXAMPLES

The compounds obtained in the examples described below are identified by the data of proton ($^1$H-NMR) and carbon-13 ($^{13}$C-NMR) magnetic nuclear resonance spectroscopy.

The magnetic nuclear resonance spectra were recorded using a Varian Gemini-200 spectrometer.

The operating frequency and the solvent used to record the spectra are indicated in the $^1$H-NMR spectra. The signal's positions are indicated in δ (ppm) and the signal from the solvent's protons is taken as a reference. The reference values were 7.24 ppm for deuterared chloroform and 2.49 ppm for hexadeuterated dimethyl sulfoxide. The signal obtained for tetramethylsilane's (TMS) protons is occasionally taken as an internal reference, with a reference value of 0 ppm. Within brackets are indicated the number of protons corresponding to each signal measured by electronic integration and the type of signal using the following abbreviations: s (singlet), d (doublet), t (triplet), q (quadruplet), dd (doublet of doublets), ddd (doublet doublet of doublets), s.b. (broad signal), cs (complex signal), s.a. $D_2O$ (simplifies upon deuteration), d.a. $D_2O$ (disappears upon deuteration).

The 13 C-NMR spectra indicate the working frequency and the solvent used to run the spectrum. The position of the signals is indicated in δ (ppm), using the central signal of the solvent as reference. The reference values are 77.00 ppm for deuterated chloroform and 39.50 ppm for hexadeuterated dimethylsulfoxide.

When HPLC analyses were performed to determine the purity or stability of some of the samples, the following conditions were used:

Symmetry C18 Column, 5 mcm, 150×3.9 mm.
Temperature: 30° C.
Eluents: A: 100% water, B: 100% acetonitrile.
Composition gradient: 0 to 100% acetonitrile in 30 min and 5 further min with 100% acetonitrile.

In the experimental part, the following abbreviations are used:

| | |
|---|---|
| AcOEt | Ethyl Acetate |
| AcOH | Acetic acid |
| DMSO-$d_6$ | Hexadeuterated dimethylsulfoxide |
| EtOH | Ethanol |
| $Et_2O$ | Diethylether |
| HPLC | High Performance Liquid Chromatography |
| IPA | Isopropylic alcohol |
| RT | Room temperature |
| THF | Tetrahydrofurane |
| TLC | Thin Layer Chromatography |

EXAMPLES

Comparative Example 1

(3R,3aS,6S,6aS)-6-(mercapto)hexahydrofuro[3,2-b]furan-3-yl nitrate

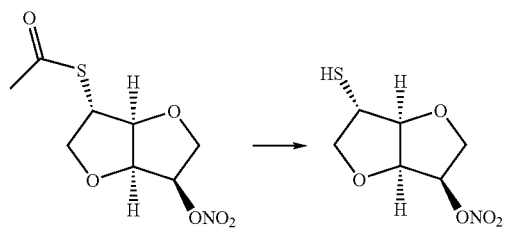

In a 500 ml flask, 10.0 g (40.2 mmol) of S-(3S,3aR,6R,6aS)-6-(nitrooxy)hexahydrofuro[3,2-b]furan-3-yl ethanethioate obtained according to WO00/20420 are dissolved in 200 mL of methyl alcohol. 100 mL of a 10% methanol solution of sodium hydroxide is added all at once. After rapidly covering and stirring for 1 min at room temperature (ca. 25° C.), 22.3 mL of concentrated hydrochloric acid are added all at once. It is stirred and concentrated to dryness, removing the solvent is reduced pressure at a temperature below 30° C.

The residue is suspended in chloroform and the solution is filtered and then dried over anhydrous magnesium sulphate. After filtration, the solvent is removed under reduced pressure and the residue is dried at reduced pressure to obtain 8.3 g of an orange-yellow oil corresponding to the title product.
Yield 100%

$^1$H-NMR (200 MHz, $CDCl_3$): 5.36-5.26 (m, 1H, $CHONO_2$), 4.95 (t, 1H, J=5.0 Hz, $CHCHONO_2$), 4.42 (d, 1H, J=4.8 Hz, CHCHS), 4.07 (dd, 1H, J=4.6 Hz, J=4.4 Hz, H—CHCHS), 3.97 (dd, 1H, J=5.6 Hz, J=2.5 Hz H—$CHCHONO_2$), 3.87-3.76 (m, 2H, H—CHCHS and H—$CHCHONO_2$), 3.45-3.35 (m, 1H, CHS), 1.77 (d, 1H, J=8.6 Hz, SH).

$^{13}$C-NMR (50 MHz, $CDCl_3$): 91.21 (CHCHS), 81.22 ($CHONO_2$), 81.07 ($CHCHONO_2$), 76.15 ($CH_2CHS$), 69.26 ($CH_2CHONO_2$), 42.82 (CHS).

Comparative Example 2

(3R,3aS,6S,6aS)-6-(benzylthio)hexahydrofuro[3,2-b]furan-3-yl nitrate

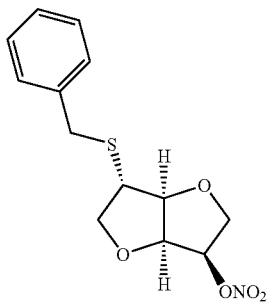

Substituting the ethyl bromide used in Example 1 (describe below) with benzyl bromide afforded the title compound.
Yield: 81% HPLC purity 97.0%

$^1$H-NMR (200 MHz, DMSO-$d_6$): 7.34-7.22 (m, 5H, Ph), 5.50-5.40 (m, 1H, $CHONO_2$), 4.94-4.86 (m, 1H, $CHCHONO_2$), 4.45-4.40 (m, 1H, CHCHS), 4.00-3.74 (m, 6H, $2CH_2O+CH_2S$), 3.24 (b.s, 1H, CHS).

$^{13}$C-NMR (50 MHz, DMSO-$d_6$): 137.90 (1C), 128.92 (2C, CH), 128.47 (2C, CH), 127.01 (1C, CH), 87.74 (CHCHS), 82.33 ($CHCHONO_2$), 81.45 ($CHONO_2$), 73.33 ($CH_2CHS$), 68.81 ($CH_2CHONO_2$), 47.90 (CHS), 34.70 ($CH_2S$).

Comparative Example 3

Ethyl 2-((3S,3aS,6R,6aS)-6-(nitrooxy)hexahydrofuro[3,2-b]furan-3-ylthio)acetate

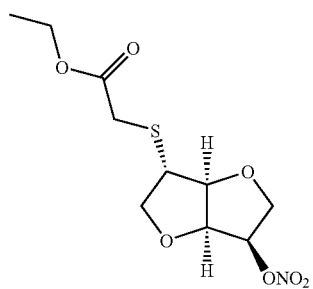

Substituting the ethyl bromide used in Example 1 (described below) with ethyl bromoacetate afforded the title compound.
Yield: 86.7% HPLC purity 98.9%

$^1$H-NMR (200 MHz, DMSO-d$_6$): 5.50-5.40 (m, 1H, CHONO$_2$), 4.91 (t, 1H, J=5.8 Hz, CHCHONO$_2$), 4.48 (d, 1H, J=4 Hz, CHCHS), 4.11 (q, 2H, OCH$_2$—CH$_3$), 4.02-3.78 (m, 4H, CH$_2$O), 3.51 (d, 1H, J=4 Hz, CHS), 3.49 (s, 2H, CH$_2$S), 1.20 (t, 3H, J=7.8 Hz, CH$_3$).

$^{13}$C-NMR (50 MHz, DMSO-d$_6$): 169.84 (CO), 87.61 (CHCHS), 82.35 (CHCHONO$_2$), 81.38 (CHONO$_2$), 73.26 (CH$_2$CHS), 68.87 (CH$_2$CHONO$_2$), 60.91 (CH$_2$O), 48.76 (CHS), 32.51 (CH$_2$S), 13.99 (CH$_3$).

Following a process similar to that described in Example 4 (described below) and starting from the products of comparative examples 2-3, the following products were obtained:

Comparative Example 4

(3R,3aS,6S,6aS)-6-((R,S)-benzylsulfinyl)hexahydro-furo[3,2-b]furan-3-yl nitrate

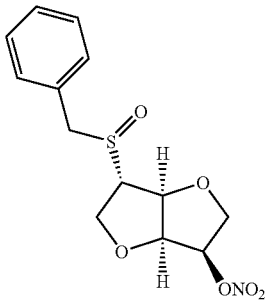

Yield: 73% HPLC purity 91.3% as a mixture of diastereoisomers 40/60

$^1$H-NMR (200 MHz, DMSO-d$_6$): 7.34 (b.s., 5H, Ph), 5.53-5.42 (m, 1H, CHONO$_2$), 4.91 (b.s, 1H, CHCHONO$_2$), 4.89 (b.s, 0.5H, CHCHS R enantiomer) 4.70-4.60 (m, 0.5H, CHCHS S enantiomer), 4.30-3.90 (m, 6H, 2H CH$_2$CHONO$_2$+2H CH$_2$CHS+2H CH$_2$S), 3.70-3.50 (m, 1H, CHS).

$^{13}$C-NMR (50 MHz, DMSO-d$_6$): 131.22 and 131.02 (1C), 130.41 (2C, CH), 128.58 (2C, CH), 127.97 (1C, CH), 83.24, 82.20 and 82.01 corresponding to CHCHONO$_2$, CHCHS and CHONO$_2$, 69.58 (CH$_2$CHS from R enantiomer), 68.94 (CH$_2$CHS from S enantiomer), 68.94 (CH$_2$CHONO$_2$ from R enantiomer), 67.11 (CH$_2$CHONO$_2$ from S enantiomer), 64.04 (CHS from S enantiomer), 63.81 (CHS from R enantiomer), 56.08 (CH$_2$S from R enantiomer) and 55.32 (CH$_2$S from S enantiomer).

Comparative Example 5

Ethyl 2-((R,S)-(3S,3aS,6R,6aS)-6-(nitrooxy)hexahydrofuro[3,2-b]furan-3-yl)sulfinyl)acetate

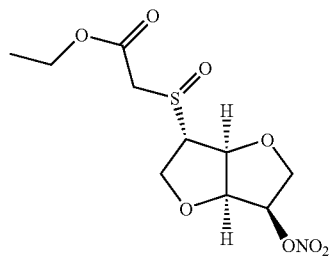

Yield: 84% HPLC purity: 98.0% as a 47/53 mixture of diastereoisomers $^1$H-NMR (200 MHz, DMSO-d$_6$): 5.53-5.46 (m, 1H, CHONO$_2$), 4.90 (b.s, 1H, CHCHONO$_2$), 4.90 (b.s, 0.5H, CHCHS R enantiomer) 4.71 (d, 0.5H, CHCHS S enantiomer), 4.30-3.80 (m, 9H, 2H CH$_2$CHONO$_2$+2H CH$_2$CHS+2H CH$_2$S+1H, CHSO+CH$_2$O), 1.22 (t, 3H, CH$_3$).

$^{13}$C-NMR (50 MHz, DMSO-d$_6$): 165.94 and 165.81 (1C, CO), 82.88 and 81.92 corresponding to CHCHONO$_2$, CHCHS and CHONO$_2$, 69.41 (CH$_2$CHS from R enantiomer), 68.94 (CH$_2$CHS from S enantiomer), 68.83 (CH$_2$CHONO$_2$ from R enantiomer), 67.04 (CH$_2$CHONO$_2$ from S enantiomer), 64.47 (CHS from S enantiomer), 64.35 (CHS from R enantiomer), 61.41 (CH$_2$O) 55.09 (CH$_2$S from R enantiomer) and 54.35 (CH$_2$S from S enantiomer), 13.93 (1C, CH$_3$).

Comparative Example 6

(3R,3aS,6S,6aS)-6-((R)-methylsulfinyl)hexahydro-furo[3,2-b]furan-3-yl nitrate

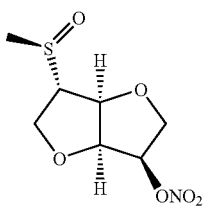

13

Process 1

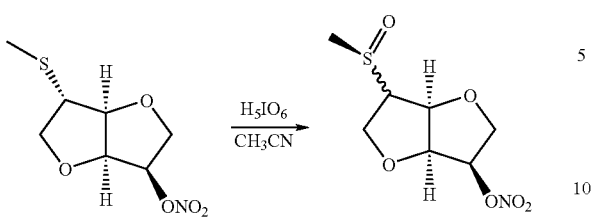

Following a process similar to that described in Example 4 (described below) and starting with 7.3 g (32.9 mmol) of (3R,3aS,6S,6aS)-6-(methylthio)hexahydrofuro[3,2-b]furan-3-yl nitrate (product described in example 3 of patent application WO2005/037842), 6.6 g of a reaction crude were obtained containing a 65/35 mixture of diastereoisomers.

The resulting reaction crude was recrystallized twice from dioxane to obtain 2.9 of the title product with a purity of 95% by HPLC.

Process 2

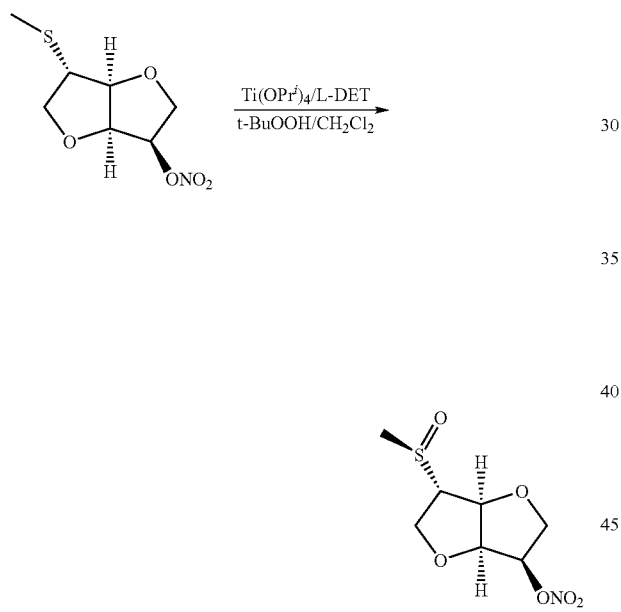

To a mixture of 12.86 g (45.25 mmol) of Titanium(IV) isopropoxide and 18.66 g (90.5 mmol) of (+)-diethyl L-tartrate (L-DET) in 75 ml of dichloromethane, were added 10 g (45.25 mmol) of (3R,3aS,6S,6aS)-6-(methylthio)hexahydrofuro[3,2-b]furan-3-yl nitrate (product described in example 3 of patent application WO2005/037842). The solution is cooled to −40° C. and 8 ml (44 mmol) of tert-butyl hydroperoxide are added and stirred for 50 h at −40° C. and 20 h at room temperature. After filtration of the inorganic salts the filtrate is concentrated under reduced pressure and the resulting residue is treated with 100 ml of diethyl ether and stirred to obtain a solid that is filtered to give 6.3 g (60%) of the title product.

$^1$H-NMR (200 MHz, DMSO-$d_6$): 5.54-5.49 (m, 1H, CHONO$_2$), 4.95-4.85 (m, 2H, CHCHONO$_2$+CHCHS), 4.15-3.89 (m, 4H, 2H CH$_2$CHONO$_2$+2H CH$_2$CHS), 3.64-3.59 (m, 1H, CHSO), 2.63 (s, 3H, CH$_3$S).

14

$^{13}$C-NMR (50 MHz, DMSO-$d_6$): 82.04 and 82.00 corresponding to CHCHONO$_2$, CHCHS and CHONO$_2$, 69.29 (CH$_2$CHS), 68.89 (CH$_2$CHS), 65.66 (CHS), 36.79 (CH$_3$S).

Comparative Example 7

(3R,3aS,6S,6aS)-6-((S)-methylsulfinyl)hexahydrofuro[3,2-b]furan-3-yl nitrate

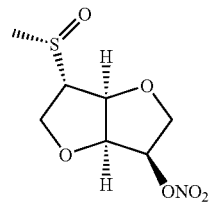

Using the mother liquors from the first recrystallization in the process 1 of comparative example 6, the solvent was removed under reduced pressure and the resulting residue recrystallized from dioxane to obtain 1 g of the title compound with a purity of 95% by HPLC.

$^1$H-NMR (200 MHz, DMSO-$d_6$): 5.54-5.49 (m, 1H, CHONO$_2$), 4.88 (t, 1H, CHCHONO$_2$), 4.67 (d, 1H, CHCHS), 4.21 (dd, 1H, H—CHCHS), 4.08-3.85 (m, 3H, 2H CH$_2$CHONO$_2$+1H H—CHCHS), 3.64-3.59 (m, 1H, CHSO), 2.58 (s, 3H, CH$_3$S).

$^{13}$C-NMR (50 MHz, DMSO-$d_6$): 82.69 and 82.04 corresponding to CHCHONO$_2$, CHCHS and CHONO2, 68.82 (CH$_2$CHS), 67.32 (CH$_2$CHS), 65.84 (CHS), 35.99 (CH$_3$S).

Following a process similar to one of the processes described in Example 7 and starting from the products of comparative examples 2-5, the following products were obtained:

Comparative Example 8

(3R,3aS,6S,6aS)-6-(benzylsulfonyl)hexahydrofuro[3,2-b]furan-3-yl nitrate

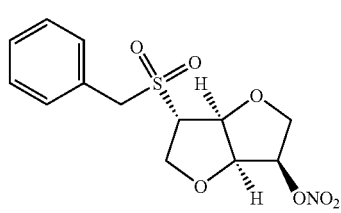

Yield: 86% HPLC purity: 98.3%

$^1$H-NMR (200 MHz, DMSO-$d_6$): 7.41 (b.s., 5H, Ph), 5.54-5.46 (m, 1H, CHONO$_2$), 4.92 (b.s., 2H, CHCHONO2+CHCHS), 4.64 (s, 2H, CH$_2$S), 4.36 (d, 1H, J=9.8 Hz, CHS), 4.08-3.85 (m, 4H, 2H CH$_2$CHONO$_2$+2H CH$_2$CHS).

$^{13}$C-NMR (50 MHz, DMSO-$d_6$): 131.95 (2C, CH), 129.55 (1C, CH), 129.03 (2C, CH), 127.70 (1C), 82.79 (CHCHS), 82.33 (CHCHONO$_2$), 81.75 (CHONO$_2$), 68.94 (CH$_2$CHS), 68.22 (CH$_2$CHONO$_2$), 65.76 (CHS), 57.18 (CH$_2$S).

Comparative Example 9

Ethyl 2-((R,S)-(3S,3aS,6R,6aS)-6-(nitrooxy)hexahydrofuro[3,2-b]furan-3-yl)sulfonyl)acetate

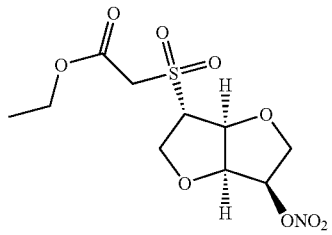

Yield: 54% HPLC purity 95.5%

$^1$H-NMR (200 MHz, DMSO-d$_6$): 5.54-5.46 (m, 1H, CHONO$_2$), 5.02 (d, 1H, J=5 Hz CHCHONO$_2$), 4.92 (t, 1H, J=5.6 HZ, CHCHS), 4.60 (d, 2H, J=4 Hz, CH$_2$S), 4.43 (d, 1H, J=11 Hz, CHS), 4.30-3.89 (m, 6H, 2H CH$_2$CHONO$_2$+2H CH$_2$CHS+OCH$_2$), 1.22 (t, 3H, J=7.2 Hz, CH$_3$).

$^{13}$C-NMR (50 MHz, DMSO-d$_6$): 162.73 (1C, CO), 82.52 ( CHCHS), 82.34 (CHCHONO$_2$), 81.73 (CHONO$_2$), 68.97 ( CH$_2$CHS), 68.08 (CH$_2$CHONO$_2$), 67.47 (CHS), 61.87 (O CH$_2$), 56.60 (CH$_2$S), 13.77 (CH$_3$).

Comparative Example 10

(3R,3aS,6S,6aS)-6-(butylthio)hexahydrofuro[3,2-b]furan-3-yl nitrate

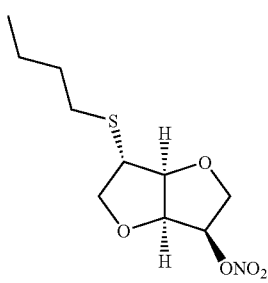

Substituting the ethyl bromide used in Example 1 (described below) with 1-bromobutane afforded the title compound.

Yield: 53% HPLC purity: 92.1%

$^1$H-NMR (200 MHz, DMSO-d$_6$): 5.50-5.40 (m, 1H, CHONO$_2$), 4.90 (t, 1H, J=5.8 Hz, CHCHONO$_2$), 4.42 (d, 1H, J=4 Hz, CHCHS), 4.02-3.76 (m, 4H, CH$_2$O), 3.38 (d, 1H, J=4 Hz, CHS), 2.59 (t, 2H, CH$_2$S), 1.60-1.45 (m, 2H, CH$_2$), 1.44-1.25 (m, 2H, CH$_2$), 0.87 (t, 3H, J=7.8 Hz, CH$_3$).

$^{13}$C-NMR (50 MHz, DMSO-d$_6$): 88.21 (CHCHS), 82.36 ( CHCHONO$_2$), 81.42 (CHONO$_2$), 73.62 (CH$_2$CHS), 68.79 ( CH$_2$CHONO$_2$), 48.17 (CHS), 31.03 (CH$_2$S), 30.30 (CH$_2$), 21.34 (CH$_2$), 13.47 (CH$_3$).

Comparative Example 11

(3R,3aS,6S,6aS)-6-((R,S)-butylsulfinyl)hexahydrofuro[3,2-b]furan-3-yl nitrate

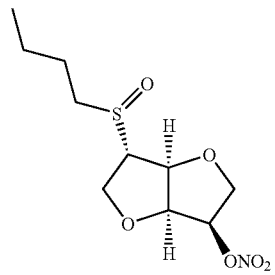

The product is obtained following a process similar to the one described in Example 4 (described below) and starting from the product of comparative example 10.

Yield: 60% HPLC purity: 93.1% as a 53/47 mixture of diastereoisomers $^1$H-NMR (200 MHz, DMSO-d$_6$): 5.53-5.46 (m, 1H, CHONO$_2$), 4.87 (b.s, 1H, CHCHONO$_2$), 4.89 (b.s, 0.5H, CHCHS R enantiomer) 4.63 (d, 0.5H, CHCHS S enantiomer), 4.25-4.15 (dd, 0.5H, H—CHCHS from S enantiomer), 4.05-3.84 (m, 3.5H, 2H CH$_2$CHONO$_2$+0.5H H—CHCHS from R enantiomer+1H H—CHCHS), 3.67-3.55 (m, 1H, CHSO), 2.90-2.60 (m, 2H, CH$_2$S), 1.75-1.55 (m, 2H, CH$_2$), 1.45-1.30 (m, 2H, CH$_2$), 0.91 (t, 3H, CH$_3$).

$^{13}$C-NMR (50 MHz, DMSO-d$_6$): 83.08 and 82.00 corresponding to CHCHONO$_2$, CHCHS and CHONO$_2$, 69.66 ( CH$_2$CHS from R enantiomer), 68.87 (CH$_2$CHS from S enantiomer), 68.87 (CH$_2$CHONO$_2$ from R enantiomer), 67.32 ( CH$_2$CHONO$_2$ from S enantiomer), 64.51 (CHS from S enantiomer), 64.15 (CHS from R enantiomer), 49.80 (CH$_2$S from R enantiomer) and 49.20 (CH$_2$S from S enantiomer), 24.57 and 24.29 (1C, CH$_2$), 21.35 (1C, CH$_2$), 13.60 (1C, CH$_3$).

Comparative Example 12

(3R,3aS,6S,6aS)-6-(butylsulfonyl)hexahydrofuro[3,2-b]furan-3-yl nitrate

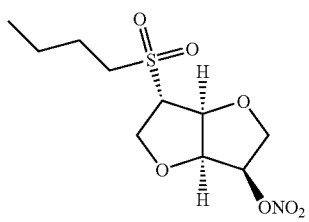

The product is obtained following a process similar to the one described in Example 7 (described below) starting from the products of comparatives examples 10 or 11.

HPLC purity: 92.3%

¹H-NMR (200 MHz, DMSO-d₆): 5.54-5.46 (m, 1H, CHONO₂), 4.96-4.86 (m, 2H, CHCHONO₂+CHCHS), 4.36 (d, 1H, J=9.8 Hz, CHS), 4.12-3.85 (m, 4H, 2H CH₂CHONO₂+2H CH₂CHS), 3.21 (t, 2H, J=7.6 Hz, CH₂S), 1.72-1.58 (m, 2H, CH₂), 1.48-1.30 (m, 2H, CH₂), 0.89 (t, 3H, J=7.6 Hz CH₃).

¹³C-NMR (50 MHz, DMSO-d₆): 82.86 (CHCHS), 82.39 (CHCHONO₂), 81.77 (CHONO₂), 68.91 (CH₂CHS), 68.39 (CH₂CHONO₂), 66.20 (CHS), 50.65 (CH₂S), 22.60 (CH₂), 21.03 (CH₂), 13.48 (CH₃).

Example 1

Synthesis of (3R,3aS,6S,6aS)-6-(ethylthio)hexahydrofuro[3,2-b]furan-3-yl nitrate

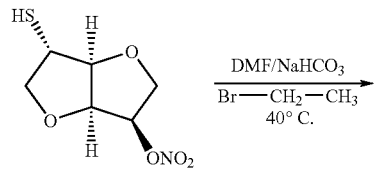

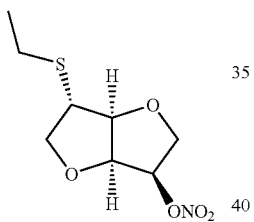

In a 100 mL flask, 4.14 g (0.02 mol) of the product of comparative example 1 and 2.99 mL (0.04 mol) of ethyl bromide were dissolved in 50 mL of dimethyl formamide (DMF) and 1.85 g (0.022 mol) of sodium hydrogen carbonate were added. The reaction mixture was stirred at 40° C. overnight and then 500 mL of water were added and extracted with 3×100 ml of ethyl acetate. The organic phase was dried, filtered and concentrated and after subjecting the crude reaction product to silica gel column chromatography on silica gel and eluting with a 8/2 mixture of hexane/ethyl acetate, after concentrating to dryness, 3.06 g of the title compound were obtained as a white solid.

Yield: 65% HPLC purity: 94.6%

¹H-NMR (200 MHz, DMSO-d₆): 5.52-5.40 (m, 1H, CHONO₂), 4.89 (t, 1H, J=5.8 Hz, CHCHONO₂), 4.42 (d, 1H, J=4 Hz, CHCHS), 4.02-3.76 (m, 4H, CH₂O), 3.41 (d, 1H, J=4 Hz, CHS), 2.59 (q, 2H, J=7.8 Hz, CH₂S), 1.19 (t, 3H, J=7.8 Hz, CH₃).

¹³C-NMR (50 MHz, DMSO-d₆): 88.18 (CHCHS), 82.35 (CHCHONO₂), 81.42 (CHONO₂), 73.58 (CH₂CHS), 68.78 (CH₂CHONO₂), 47.78 (CHS), 24.60 (CH₂S), 14.55 (CH₃)

Starting from (3R,3aS,6S,6aS)-6-mercaptohexahydrofuro[3,2-b]furan-3-yl nitrate (Comparative Example 1) and replacing ethyl bromide with the corresponding alkyl halide and following a process similar to that described in Example 1, the following products were obtained:

Example 2

(3R,3aS,6S,6aS)-6-(propylthio)hexahydrofuro[3,2-b]furan-3-yl nitrate

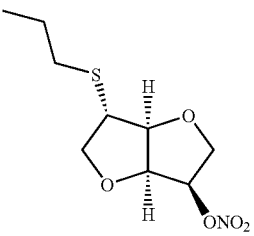

Substituting the ethyl bromide used in Example 1 with 1-bromopropane afforded the title compound.

Yield: 60% HPLC purity: 96.2%

¹H-NMR (200 MHz, DMSO-d₆): 5.52-5.40 (m, 1H, CHONO₂), 4.90 (t, 1H, J=5.8 Hz, CHCHONO₂), 4.42 (d, 1H, J=4 Hz, CHCHS), 4.02-3.76 (m, 4H, CH₂O), 3.38 (d, 1H, J=4 Hz, CHS), 2.55 (t, 2H, CH₂S), 1.65-1.45 (m, 2H, CH₂), 0.93 (t, 3H, J=7.8 Hz, CH₃).

¹³C-NMR (50 MHz, DMSO-d₆): 88.23 (CHCHS), 82.36 (CHCHONO₂), 81.43 (CHONO₂), 73.64 (CH₂CHS), 68.80 (CH₂CHONO₂), 48.10 (CHS), 32.64 (CH₂S), 22.32 (CH₂), 13.22 (CH₃).

Example 3

(3R,3aS,6S,6aS)-6-(allylthio)hexahydrofuro[3,2-b]furan-3-yl nitrate

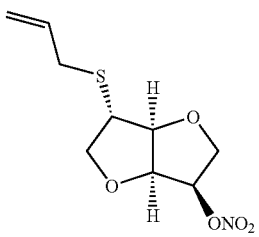

Substituting the ethyl bromide used in Example 1 with allyl bromide the title product was obtained.

Yield: 87% HPLC purity: 99.3%

¹H-NMR (200 MHz, DMSO-d₆): 5.90-5.70 (m, 1H, CH=CH₂), 5.46 (t, 1H, CHONO₂), 5.20-5.10 (m, 2H, CH=CH₂), 4.90 (t, 1H, J=5.8 Hz, CHCHONO₂), 4.43 (d, 1H, J=4 Hz, CHCHS), 4.02-3.76 (m, 4H, CH₂O), 3.30-3.20 (m, 3H, CHS+CH₂S).

$^{13}$C-NMR (50 MHz, DMSO-d$_6$): 134.13 (_C_H=CH$_2$), 117.67 (CH=_C_H$_2$), 87.92 (_C_HCHS), 82.37 (_C_HCHONO$_2$), 81.44 (CHO_N_O$_2$), 73.43 (_C_H$_2$CHS), 68.84 (_C_H$_2$CHONO$_2$), 47.41 (_C_HS), 33.56 (_C_H$_2$S).

Example 4

(3R,3aS,6S,6aS)-6-((R,S)-ethylsulfinyl)hexahydro-furo[3,2-b]-furan-3-yl nitrate

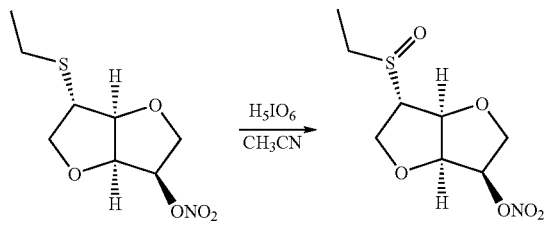

To a solution of 0.71 g (3 mmol) of the product obtained in example 1 in 50 ml of acetonitrile were added 0.75 g (3.3 mmol) of periodic acid. The reaction was stirred at room temperature during 48 h followed by addition of a saturated solution of sodium thiosulfate and then the reaction product extracted with 3×100 ml of dichloromethane. The organic phase was dried, filtered and concentrated and after subjecting the crude reaction product to silica gel column chromatography and eluting with a 99/1 mixture of dichloromethane/methyl alcohol, after concentrating to dryness, 320 mg of the title compound were obtained as a white solid.

Yield: 43% HPLC purity: 99.35% as a 51/49 mixture of diastereoisomers $^1$H-NMR (200 MHz, DMSO-d$_6$): 5.53-5.46 (m, 1H, C_H_ONO$_2$), 4.89 (t, 1H, J=5.8 Hz, C_H_CHONO$_2$), 4.89 (d, 0.5H, C_H_CHS R enantiomer) 4.42 (d, 0.5H, C_H_CHS S enantiomer), 4.26 (dd, 0.5H, H—CHCHS from S enantiomer), 4.02-3.76 (m, 3.5H, 2H CH$_2$CHONO$_2$+0.5H H—CHCHS from R enantiomer+1H H—CHCHS), 3.64-3.57 (m, 1H, C_H_SO), 2.90-2.55 (m, 2H, C_H_$_2$S), 1.22 (dt, 3H, C_H_$_3$).

$^{13}$C-NMR (50 MHz, DMSO-d$_6$): 83.83, 82.82 and 82.78 corresponding to _C_HCHONO$_2$, _C_HCHS and _C_HONO$_2$, 70.35 (_C_H$_2$CHS from R enantiomer), 69.61 (_C_H$_2$CHS from S enantiomer), 69.56 (_C_H$_2$CHONO$_2$ from R enantiomer), 68.09 (_C_H$_2$CHONO$_2$ from S enantiomer), 64.79 (_C_HS from S enantiomer), 64.44 (_C_HS from R enantiomer), 44.44 (_C_H$_2$S from R enantiomer) and 43.86 (_C_H$_2$S from S enantiomer), 7.65 and 7.36 (1C, _C_H$_3$)

Following a process similar to the one described in Example 4 and starting from the products of examples 2-3, the following products were obtained:

Example 5

(3R,3aS,6S,6aS)-6-((R,S)-propylsulfinyl)hexahydro-furo[3,2-b]furan-3-yl nitrate

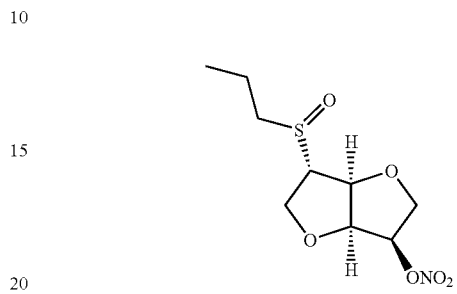

Yield: 81% HPLC purity: 97.9% as a 46/54 mixture of diastereoisomers $^1$H-NMR (200 MHz, DMSO-d$_6$): 5.53-5.46 (m, 1H, C_H_ONO$_2$), 4.87 (b.s, 1H, C_H_CHONO$_2$), 4.89 (b.s, 0.5H, C_H_CHS R enantiomer), 4.65 (d, 0.5H, C_H_CHS S enantiomer), 4.30-4.15 (d, 0.5H, H—CHCHS from S enantiomer), 4.05-3.76 (m, 3.5H, 2H CH$_2$CHONO$_2$+0.5H H—CHCHS from R enantiomer+1H H—CHCHS), 3.64-3.55 (m, 1H, C_H_SO), 2.75 (t, 2H, C_H_$_2$S), 1.75-1.55 (m, 2H, C_H_$_2$), 1.00 (t, 3H, C_H_$_3$).

$^{13}$C-NMR (50 MHz, DMSO-d$_6$): 83.04 and 82.00 corresponding to _C_HCHONO$_2$, _C_HCHS and _C_HONO$_2$, 69.62 (_C_H$_2$CHS from R enantiomer), 68.89 (_C_H$_2$CHS from S enantiomer), 68.89 (_C_H$_2$CHONO$_2$ from R enantiomer), 67.33 (_C_H$_2$CHONO$_2$ from S enantiomer), 64.51 (_C_HS from S enantiomer), 64.17 (_C_HS from R enantiomer), 51.93 (_C_H$_2$S from R enantiomer) and 51.33 (_C_H$_2$S from S enantiomer), 16.21 and 15.93 (1C, _C_H$_2$), 13.04 (1C, _C_H$_3$)

Example 6

(3R,3aS,6S,6aS)-6-((R,S)-allylsulfinyl)hexahydro-furo[3,2-b]furan-3-yl nitrate

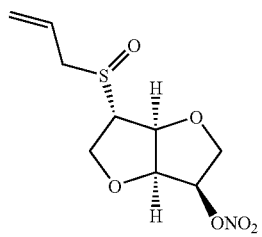

Yield: 62% HPLC purity: 95.1% as a 44/56 mixture of diastereoisomers $^1$H-NMR (200 MHz, DMSO-d$_6$): 6.00-5.75 (m, 1H, C_H_=CH$_2$), 5.53-5.30 (m, 3H, CH=C_H_$_2$+C_H_ONO$_2$), 4.95-4.83 (m, 1, 5H, C_H_CHONO$_2$+0.5H C_H_CHS R enantiomer), 4.65-4.60 (m, 0.5H, C_H_CHS S enantiomer), 4.30-4.20 (d, 0.5H, H—CHCHS from S enantiomer), 4.10-3.70 (m, 3.5H, 2H CH$_2$CHONO$_2$+0.5H H—CHCHS from R enantiomer+1H H—CHCHS), 3.64-2.90 (m, 3H, C_H_SO+C_H_$_2$S).

¹³C-NMR (50 MHz, DMSO-d₆): 127.26 and 127.08 (CH=CH₂), 123.45 (CH=CH₂) 83.17, 82.16 and 82.00 corresponding to CHCHONO₂, CHCHS and CHONO₂, 69.65 (CH₂CHS from R enantiomer), 68.91 (CH₂CHS from S enantiomer), 68.91 (CH₂CHONO₂ from R enantiomer), 67.21 (CH₂CHONO₂ from S enantiomer), 63.84 (CHS from S enantiomer), 63.53 (CHS from R enantiomer), 54.21(CH₂S from R enantiomer) and 53.55 (CH₂S from S enantiomer)

Example 7

(3R,3aS,6S,6aS)-6-(ethylsulfonyl)hexahydrofuro[3,2-b]furan-3-yl nitrate

Process 1

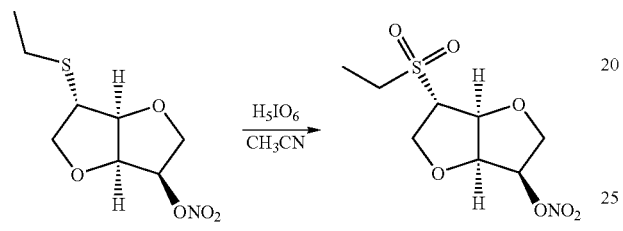

To a solution of 0.71 g (3 mmol) of the product obtained in example 1 in 50 ml of acetonitrile were added 2.05 g (9 mmol) of periodic acid. The reaction was stirred at room temperature for 48 h and then a saturated solution of sodium thiosulfate was added and the reaction product extracted with 3×100 ml of dichloromethane. The organic phase was dried, filtered and concentrated and the crude reaction was stirred with 40 ml of 2-propanol to obtain a white solid that was filtered to give 550 mg of the title compound.
Yield: 68% HPLC purity: 99.5%
Process 2

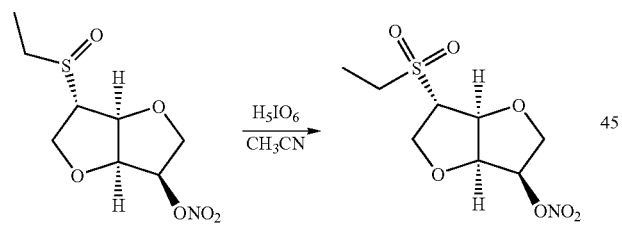

To a solution of 0.75 g (3 mmol) of the product obtained in example 4 in 50 ml of acetonitrile were added 0.75 g (3.3 mmol) of periodic acid. The reaction was stirred at room temperature for 48 h and then a saturated solution of sodium thiosulfate was added and the reaction product extracted with 3×100 ml of dichloromethane. The organic phase was dried, filtered and concentrated and after subjecting the crude reaction product to silica gel column chromatography and eluting with a 1/1 mixture of hexane/diethyl acetate, after concentrating to dryness, 620 mg of the title compound were obtained as a white solid.
Yield: 77% HPLC purity: 98.5%
¹H-NMR (200 MHz, DMSO-d₆): 5.51-5.46 (m, 1H, CHONO₂), 4.95-4.88 (m, 2H, CHCHONO₂+CHCHS), 4.36 (d, 1H, J=9.8 Hz, CHS), 4.12-3.88 (m, 4H, 2H CH₂CHONO₂+2H CH₂CHS), 3.21 (q, 2H, J=7.4 Hz, CH₂S), 1.22 (t, 3H, J=7.4 Hz CH₃).

¹³C-NMR (50 MHz, DMSO-d₆): 82.85 (CHCHS), 82.30 (CHCHONO₂), 81.67 (CHONO₂), 68.83 (CH₂CHS), 68.35 (CH₂CHONO₂), 65.54 (CHS), 45.61 (CH₂S), 5.44 (CH₃).

Following a process similar to the one described in Example 7 and starting from the products of examples 2-3 and 5-6, the following products were obtained:

Example 8

(3R,3aS,6S,6aS)-6-(propylsulfonyl)hexahydrofuro[3,2-b]furan-3-yl nitrate

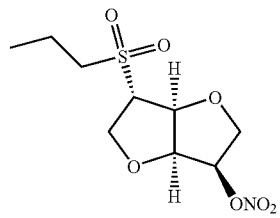

HPLC purity: 94.2%
¹H-NMR (200 MHz, DMSO-d₆): 5.51-5.46 (m, 1H, CHONO₂), 4.93 (b.s., 2H, CHCHONO₂+CHCHS), 4.36 (d, 1H, J=9.8 Hz, CHS), 4.12-3.85 (m, 4H, 2H CH₂CHONO₂+2H CH₂CHS), 3.19 (t, 2H, J=7.6 Hz, CH₂S), 1.80-1.60 (m, 2H, CH₂), 0.99 (t, 3H, J=7.6 Hz CH₃).
¹³C-NMR (50 MHz, DMSO-d₆): 82.86 (CHCHS), 82.37 (CHCHONO2), 81.74 (CHONO₂), 68.99 (CH₂CHS), 68.38 (CH₂CHONO₂), 66.20 (CHS), 52.53 (CH₂S), 14.56 (CH₂), 12.83 (CH₃).

Example 9

(3R,3aS,6S,6aS)-6-(allylsulfonyl)hexahydrofuro[3,2-b]furan-3-yl nitrate

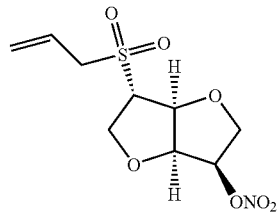

HPLC purity: 88.4%
¹H-NMR (200 MHz, DMSO-d₆): 5.94-5.72 (m, 1H, CH=CH₂), 5.55-5.40 (m, 3H, CH=CH₂+CHONO₂), 5.00-4.85 (m., 2H, CHCHONO₂+CHCHS), 4.37 (d, 1H, J=9.8 Hz, CHS), 4.12-3.85 (m, 6H, 2H CH₂CHONO₂+2H CH₂CHS+2H SCH₂).

$^{13}$C-NMR (50 MHz, DMSO-d$_6$): 125.12 (CH=CH$_2$), 124.52 (CH=CH$_2$), 82.78 (CHCHS), 82.34 (CHCHONO$_2$), 81.73 (CHONO$_2$), 68.92 (CH$_2$CHS), 68.29 (CH$_2$CHONO$_2$), 65.67 (CHS), 56.03 (CH$_2$S).

Example 10

Synthesis of S-(3R,3aS,6R,6aS)-6-(nitrooxy)hexahydrofuro[3,2-b]furan-3-yl ethanethioate

10a. Synthesis of (3S,3aS,6R,6aR)-6-hydroxyhexahydrofuro[3,2-b]furan-3-yl 4-methylbenzenesulfonate

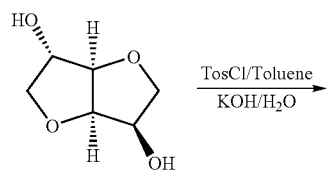

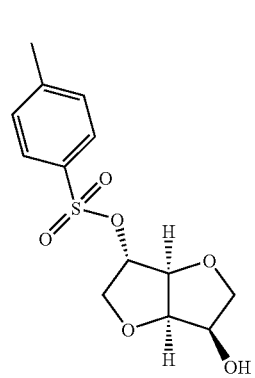

In a 2 L flask, 100.0 g (0.684 mol) of (3R,3aR,6S,6aR)-hexahydrofuro[3,2-b]furan-3,6-diol (Isosorbide) were dissolved in 600 ml of water and 130, 5 g (0.684 mol) of Tosyl chloride dissolved in 600 ml of Toluene are added at 0° C. 49.5 g (0.751 mol) of potassium hydroxide (86%) in 170 ml of water were added dropwise over ½ h at 0° C. and the reaction was stirred for 1 hr at 0° C. and 5 h at room temperature. The organic phase was extracted, dried, filtered and concentrated under vacuum and after subjecting the crude reaction product to silica gel column chromatography and eluting with a 99/1 mixture of dichloromethane/methyl alcohol, 50.0 g of the product of the title were obtained after concentrating to dryness.

$^1$H-NMR (200 MHz, DMSO-d$_6$): 7.82 (d, 2H, J=8.4 HZ, 2o-H), 7.48 (d, 2H, J=8.4 HZ, 2m-H), 4.98 (d, 1H, OH), 4.78 (s, 1H, CHOTos), 4.48-4.35 (m, 2H, CHCHOH+CHCHOTos), 4.15-4.00 (m, 1H, CHOH), 3.81 (d, 1H, J=2.2 Hz, CH$_2$CHOTos), 3.69 (t, 1H, H—CHCHOH), 3.28 (t, 1H, H—CHCHOH), 2.42 (s, 3H, CH$_3$).

$^{13}$C-NMR (50 MHz, DMSO-d$_6$): 145.35 (1C, C—SO$_2$—), 132.62 (1C, C—CH$_3$), 130.35 (2C, CH), 127.62 (2C, CH), 84.81 (CHCHOS$_2$—), 84.55 (CHOSO$_2$), 81.60 (CHCHOH), 72.28 (CH$_2$CHOSO$_2$—), 71.57 (CH$_2$CHOH), 71.48 (CHOH), 21.11 (CH$_3$).

10b. Synthesis of (3S,3aS,6R,6aR)-6-(tetrahydro-2H-pyran-2-yloxy)hexahydrofuro[3,2-b]furan-3-yl 4-methylbenzenesulfonate

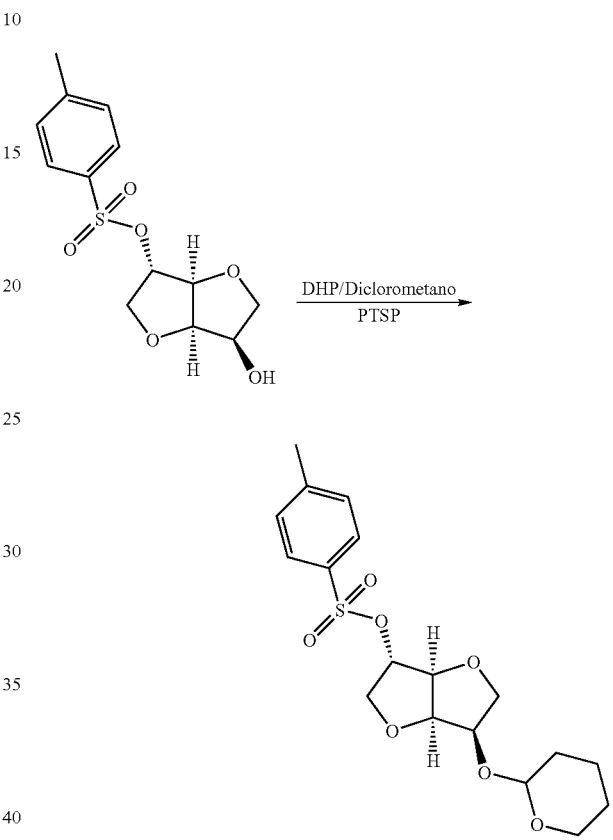

In a 1 L flask, 50.0 g (0.166 mol) of the product obtained in 10a were dissolved in 550 ml of dichloromethane at 0° C. and 45.3 mL (0.499 mol) of 3,4-dihydro-2H-pyran were added dropwise over ½ h and then 9.35 g (0.037 mol) of p-Toluenesulfonic acid pyridinium salt (PTSP) were added at 0° C. and the reaction was stirred for 1 hr at 0° C. and 4 h at room temperature.

The organic phase was washed with 4×400 mL of water and then the organic phase was dried, filtered and concentrated under vacuum to give 74.3 g of a crude that was used in the next step without purification.

$^1$H—RMN (DMSO-d$_6$, 200 MHz): 7.82 (d, 2H, J=8.0 Hz, o-CH$_{ar}$), 7.48 (d, 2H, J=8.2 Hz, m-CH$_{ar}$), 4.80 (s, 1H, CHCHOTHP), 4.66-4.43 (sc, 2H, CHOTos, CH$_{THP}$), 4.45-4.35 (m, 1H, CHCHOTos), 4.15-4.05 (m, 1H, CHOTHP), 3.85-3.75 (sc, 4H, CH$_2$CHOTos, CH$_2$O$_{THP}$), 3.50-3.30 (sc, 2H, CH$_2$CHOTHP), 2.41 (s, 3H, CH$_3$), 1.80-1.27 (sc, 6H, 3CH$_2$ $_{THP}$).

$^{13}$C-RMN (DMSO-d$_6$, 50 MHz): 144.3 (C$_{ar}$), 131.5 (C$_{ar}$), 129.3 (2CH$_{ar}$), 126.5 (2CH$_{ar}$), 96.8 and 96.5 (CH$_{THP}$) 83.8 and 83.7, 83.2 and 83.0 (CHOTos, CH—CHOTos,), 80.1 and 79.2 (CHCHOTHP), 75.9 and 74.3 (CHOTHP), 71.2, 69.5 and 67.6 (CH$_2$CHOTos, CH$_2$CHOTHP), 60.5 and 59.9

($CH_2O_{THP}$), 28.9 ($CH_{2\,THP}$), 23.8 ($CH_{2\,THP}$), 23.8 ($CH_{2\,THP}$), 20.0 ($CH_3$—$C_{ar}$), 17.9 and 17.5 ($CH_{2\,THP}$).

10c. Synthesis of S-(3R,3aS,6R,6aR)-6-(tetrahydro-2H-pyran-2-yloxy)hexahydrofuro[3,2-b]furan-3-yl ethanethioate

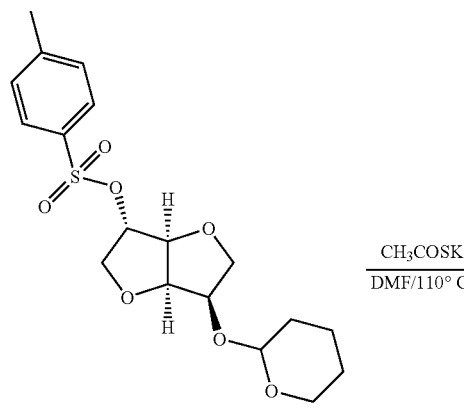

The product obtained in 10b and 66.5 g (0.582 mol) of potassium thioacetate were dissolved in 450 ml of dimethylformamide (DMF) and heated at 110° C. for 26 h. 2 L of ethyl acetate were added and the reaction mixture was washed with 4×400 mL of water and then the organic phase was dried, filtered and concentrated under vacuum.

After subjecting the crude reaction product to silica gel column chromatography and eluting with 10/1 a mixture of dichloromethane/ethyl acetate, after concentration, 16.3 g of the title compound were obtained.

$^{1}$H—RMN (DMSO-$d_6$, 200 MHz): 4.67 (s, 1H, C HCHOTHP), 4.65-4.50 (m, 1H, CHCHS), 4.60-4.45 (m, 1H, $\overline{C}HO_{THP}$), 4.30-4.10 (sc, 1H, $CH\overline{O}THP$), 3.90-3.70 (sc, 3H, $CH_2O_{THP}$, CHS), 3.60-3.50 (m, 1H, H—CH—CHS), 3.50-3.35 (sc, 2H, $CH_2$—CHOTHP), 2.32 (s, 3H, $CH_3$—$C_{ar}$), 1.80-1.27 (sc, 6H, 3$CH_2$ THP).

$^{13}$C-RMN (DMSO-$d_6$, 50 MHz): 194.0 (CO), 97.0 and 96.4 ($CH_{THP}$), 81.1 and 80.9+80.8 and 80.0 (CH—CHS, CH—CHO), 76.6 and 74.9 (CHOTHP), 71.2 and 70.9+70.3 and 68.6 ($\underline{C}H_2$—CHS, $\underline{C}H_2$—CHOTHP), 60.5 and 59.9 ($\underline{C}H_2O_{THP}$), 45.4 and 44.7 (CHS), 29.3 ($CH_{2\,THP}$), 28.9 ($CH_{2\,THP}$), 23.8 ($\underline{C}H_3CO$), 17.9 and 17.6 ($CH_{2\,THP}$).

10d. Synthesis of S-(3R,3aS,6R,6aS)-6-(nitrooxy)hexahydrofuro[3,2-b]furan-3-yl ethanethioate

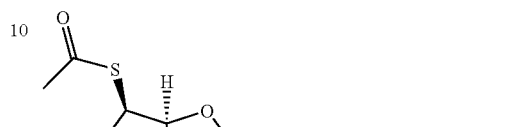

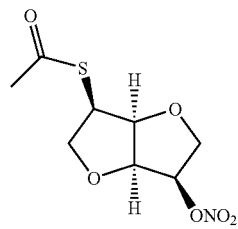

The product obtained in 10c was dissolved in 8 ml of acetic acid at 5° C. and a freshly prepared mixture of acetic acid/acetic anhydride/nitric acid 33.2 mL/7.6 mL/8.1 mL was added dropwise at 5° C. over 1 h. The reaction mixture was stirred at 5° C. for 1 h. Toluene (600 mL) was added and the reaction mixture was washed with 4×400 mL of brine, 4×400 mL of a saturated solution of sodium hydrogen carbonate and 400 mL of water. The organic phase was dried, filtered and concentrated under vacuum. After subjecting the crude reaction product to silica gel column chromatography and eluting with Toluene; after concentration, 1.3 g of the title compound were obtained.

$^{1}$H—RMN (CDCl$_3$, 200 MHz): 5.33 (ddd, 1H, J=8.4 Hz, 5.4 Hz, 2.8 Hz, CHONO$_2$), 4.91 (dd, 1H, J=4.8 Hz, 4.8 Hz, C HCHONO$_2$), 4.55 (dd, 1H, J=4.8 Hz, 4.8 Hz, CHCHS), 4.20-3.80 (m, 4H, CHS, H—CHCHS, $CH_2$—CHO$\overline{N}O_2$), 3.56 (dd, 1H, J=8.0 Hz, 11.2 Hz, H—CHCHS), 2.34 (s, 3H, $CH_3$CO).

$^{13}$C-RMN (CDCl$_3$, 50 MHz): 194.5 (C=O), 83.4 ( CHCHS), 82.2 (CH—CHONO$_2$), 81.6 (CHONO$_2$), 71.8 ( $\underline{C}H_2$—CHS), 69.6 ($CH_2$—CHONO$_2$), 44.7 (CHS), 30.4 ( $\underline{C}H_3$CO).

Starting from S-(3R,3aS,6R,6aS)-6-(nitrooxy)hexahydrofuro[3,2-b]furan-3-yl ethanethioate obtained in 10d and following a process similar to the one described in Comparative example 1, (3R,3aS,6R,6aS)-6-mercaptohexahydrofuro[3,2-b]furan-3-yl nitrate was obtained in a first step; from this the following products may be obtained following processes similar to those described for examples 1 y 2:

Example 11

(3R,3aS,6R,6aS)-6-(ethylthio)hexahydrofuro[3,2-b]furan-3-yl nitrate

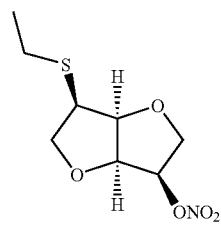

Yield: 93% HPLC purity: 91.2%

$^1$H-NMR (200 MHz, DMSO-$d_6$): 5.52-5.40 (m, 1H, CHONO$_2$), 4.86 (t, 1H, J=5.0 Hz, CHCHONO$_2$), 4.44 (t, 1H, J=4.4 Hz, CHCHS), 4.10-3.10 (m, 5H, CH$_2$CHS+CH$_2$CHONO$_2$+CHSEt), 2.55 (q, 2H, J=7.2 Hz, CH$_2$S), 0.91 (t, 3H, J=7.2 Hz, CH$_3$).

$^{13}$C-NMR (50 MHz, DMSO-$d_6$): 82.76 (CHCHS), 82.95 (CHCHONO$_2$), 82.05 (CHONO$_2$), 73.11 (CH$_2$CHONO$_2$), 68.97 (CH$_2$CHS), 46.49 (CHS), 25.46 (CH$_2$), 15.51 (CH$_3$).

Example 12

(3R,3aS,6R,6aS)-6-(propylthio)hexahydrofuro[3,2-b]furan-3-yl nitrate

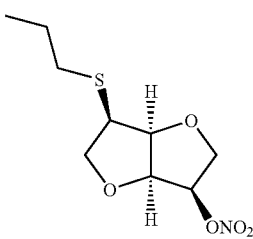

Yield: 40% HPLC purity: 96.5%

$^1$H-NMR (200 MHz, DMSO-$d_6$): 5.52-5.40 (m, 1H, CHONO$_2$), 4.85 (t, 1H, J=5.2 Hz, CHCHONO$_2$), 4.43 (t, 1H, J=4.4 Hz, CHCHS), 3.40-3.10 (m, 2H, CH$_2$CHS), 2.50 (b.s., 2H, CH$_2$S), 1.60-1.40 (m, 2H, CH$_2$), 0.91 (t, 3H, J=7.4 Hz, CH$_3$).

$^{13}$C-NMR (50 MHz, DMSO-$d_6$): 83.21 (CHCHS), 82.94 (CHCHONO$_2$), 82.06 (CHONO$_2$), 73.09 (CH$_2$CHONO$_2$), 68.97 (CH$_2$CHS), 46.77 (CHS), 33.51 (CH$_2$S), 23.16 (CH$_2$), 13.09 (CH$_3$).

Following a process similar to the one described in example 4 and starting from the products obtained in the examples 11-12, the following products were obtained:

Example 13

(3R,3aS,6R,6aS)-6-((R,S)-ethylsulfinyl)hexahydrofuro[3,2-b]furan-3-yl nitrate

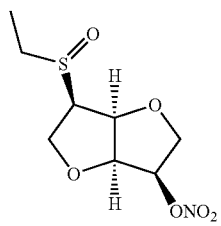

Silica gel column chromatography on silica gel of the reaction crude and elution with ethyl acetate yielded each one of the diastereomers of the title compound.

Diastereomer 1

$^1$H-NMR (200 MHz, DMSO-$d_6$): 5.50-5.42 (m, 1H, CHONO$_2$), 4.91 (t, 1H, J=5.6 Hz, CHCHONO$_2$), 4.70 (t, 1H, J=5.2 Hz, CHCHS), 4.25-3.80 (m, 4H, CH$_2$CHONO$_2$+CH$_2$CHS), 3.63-3.50 (m, 1H, CHS), 3.00-2.70 (m, 2H, CH$_2$S), 1.22 (t, 3H, J=7.8 Hz, CH$_3$).

$^{13}$C-NMR (50 MHz, DMSO-$d_6$): 82.92 (CHCHS), 82.60 (CHCHONO$_2$), 81.85 (CHONO$_2$), 69.34 (CH$_2$CHONO$_2$), 69.18 (CH$_2$CHS), 62.24 (CHS), 44.28 (CH$_2$S), 6.35 (CH$_3$).

Diastereomer 2

$^1$H-NMR (200 MHz, DMSO-$d_6$): 5.55-5.48 (m, 1H, CHONO$_2$), 4.94 (t, 1H, J=4.8 Hz, CHCHONO$_2$), 4.67 (t, 1H, J=4.0 Hz, CHCHS), 4.10-3.80 (m, 3H, CH$_2$CHONO$_2$+CHS), 3.58-3.52 (m, 2H, CH$_2$CHS), 2.70-2.55 (m, 2H, CH$_2$S), 1.19 (t, 3H, J=7.6 Hz, CH$_3$).

$^{13}$C-NMR (50 MHz, DMSO-$d_6$): 82.89 (CHCHS), 82.54 (CHCHONO$_2$+CHONO$_2$), 69.49 (CH$_2$CHONO$_2$), 66.68 (CH$_2$CHS), 64.27 (CHS), 43.89 (CH$_2$S), 6.08 (CH$_3$).

Example 14

(3R,3aS,6R,6aS)-6-((R,S)-propylsulfinyl)hexahydrofuro[3,2-b]furan-3-yl nitrate

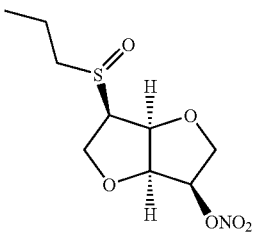

Silica gel column chromatography of the reaction crude and elution with ethyl acetate yielded each one of the diastereomers of the title compound.

Diastereomer 1

HPLC purity: 96.0%

$^{1}$H-NMR (200 MHz, CDCl$_{3}$): 5.36-5.28 (m, 1H, CHONO$_{2}$), 4.92 (t, 1H, J=5.6 Hz, CHCHONO$_{2}$), 4.72 (t, 1H, J=5.2 Hz, CHCHS), 4.45-4.25 (m, 2H, CH$_{2}$CHONO$_{2}$), 4.08-3.86 (m, 2H, CH$_{2}$CHS), 3.43-3.32 (m, 1H, CHS), 3.00-2.70 (m, 2H, CH$_{2}$S), 2.00-1.75 (m, 2H, CH$_{2}$), 1.09 (t, 3H, J=7.4Hz, CH$_{3}$).

$^{13}$C-NMR (50 MHz, CDCl$_{3}$): 82.91 (CHCHS), 82.58 (CHCHONO$_{2}$), 80.40 (CHONO$_{2}$), 70.61 (CH$_{2}$CHONO$_{2}$), 69.52 (CH$_{2}$CHS), 64.91 (CHS), 53.88 (CH$_{2}$S), 15.99 (CH$_{2}$), 13.14 (CH$_{3}$).

Diastereomer 2

HPLC purity: 95.8%

$^{1}$H-NMR (200 MHz, CDCl$_{3}$): 5.38-5.31 (m, 1H, CHONO$_{2}$), 4.93 (t, 1H, J=5.2 Hz, CHCHONO$_{2}$), 4.81 (t, 1H, J=5.2 Hz, CHCHS), 4.10 (d, 1H, J=11.4 Hz, CHS), 4.07-3.88 (m, 2H, CH$_{2}$CHONO$_{2}$), 3.76-3.39 (m, 2H, CH$_{2}$CHS), 2.75-2.40 (m, 2H, CH$_{2}$S), 1.95-1.70 (m, 2H, CH$_{2}$), 1.05 (t, 3H, J=7.4 Hz, CH$_{3}$).

$^{13}$C-NMR (50 MHz, CDCl$_{3}$): 82.64 (CHCHS), 82.45 (CHCHONO$_{2}$), 81.20 (CHONO$_{2}$), 69.82 (CH$_{2}$CHONO$_{2}$), 66.82 (CH$_{2}$CHS), 65.82 (CHS), 53.59 (CH$_{2}$S), 15.73 (CH$_{2}$), 12.98 (CH$_{3}$).

Following a process similar to the one described in example 7 and starting from the products obtained in examples 11-12 or 13-14, the following products were obtained:

Example 15

(3R,3aS,6R,6aS)-6-(ethylsulfonyl)hexahydrofuro[3,2-b]furan-3-yl nitrate

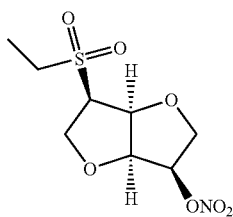

$^{1}$H-NMR (200 MHz, DMSO-d$_{6}$): 5.58-5.44 (m, 1H, CHONO$_{2}$), 4.90 (t, 1H, J=5.2 Hz, CHCHONO$_{2}$) 4.75 (t, 1H, J=4.8 Hz, CHCHS), 4.27 (t, 1H, J=7.2 Hz, CHS), 4.07-3.85 (m, 4H, CH$_{2}$CHONO$_{2}$+CH$_{2}$CHS), 3.17 (q, 2H, J=7.4 Hz, CH$_{2}$S), 1.21 (t, 3H, J=7.4 Hz, CH$_{3}$).

$^{13}$C-NMR (50 MHz, DMSO-d$_{6}$): 82.81 (CHCHS), 81.84 (CHCHONO$_{2}$), 81.68 (CHONO$_{2}$), 69.54 (CH$_{2}$CHONO$_{2}$), 67.51 (CH$_{2}$CHS), 63.26 (CHS), 48.00 (CH$_{2}$S), 5.31 (CH$_{3}$).

Example 16

(3R,3aS,6R,6aS)-6-(propylsulfonyl)hexahydrofuro[3,2-b]furan-3-yl nitrate

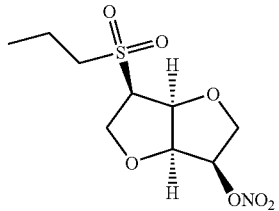

HPLC purity: 88.68%

$^{1}$H-NMR (200 MHz, CDCl$_{3}$): 5.36-5.24 (m, 1H, CHONO$_{2}$), 5.10-4.70 (m, 2H, CHCHONO$_{2}$+CHCHS), 4.45-3.90 (m, 4H, CH$_{2}$CHONO$_{2}$+CH$_{2}$CHS), 3.68 (b.s., 1H, CHS), 3.30-2.90 (m, 2H, CH$_{2}$S), 2.10-1.80 (m, 2H, CH$_{2}$), 1.10 (t, 3H, CH$_{3}$).

$^{13}$C-NMR (50 MHz, CDCl$_{3}$): 82.94 (CHCHS), 81.64 (CHCHONO$_{2}$), 80.47 (CHONO$_{2}$), 70.05 (CH$_{2}$CHONO$_{2}$), 67.99 (CH$_{2}$CHS), 66.07 (CHS), 55.74 (CH$_{2}$S), 14.65 (CH$_{2}$), 13.20 (CH$_{3}$).

Anti-Thrombotic Activity Assessment

Experimental Procedure

Male Wistar rats weighing 250-300 g were used after an acclimatization period of five days, and animals were divided in groups of 8 animals each for the treatments. In all experiments, rats were treated with 90 μmol/kg of each product by oral gavage using an administration volume of 10 ml/kg. The vehicle used to dissolve the products consisted of 1% Cremophor EL 27963, 1% Tween 80 and 0.5% Methocel E-15 in distilled water. After a fasting period of 8 hours with free access to drinking water each product was given by gavage 1 hour before induction of thrombosis.

Thrombus formation was induced using a patch embedded with 70% FeCl$_{3}$ solution applied onto the carotid artery using the same procedure described by Feuerstein G Z et al and later modified by Kurz et al (Feuerstein G Z, et al Artherioscler. Thromb. Vasc. Biol. 1999, 19: 2554-2562, Kurz K D, et al Thromb. Res. 1990, 60:269-280). Anti-thrombotic efficacy was evaluated at different times after dosage. Rats were anesthetized with sodium pentobarbital and then placed on a dorsal position over a thermal blanket laid on a surgical board and heated at 37° C. The left carotid artery was dissected and an electromagnetic blood flow probe was placed on the artery to measure blood flow. After application of the thrombotic stimuli, blood flow was monitored for the following 30 minutes. The vessel was considered occluded by the thrombus when flow reached 0.0 ml/min.

Data were analysed by contingency tables using the Graph Pad Prism Program. P values were calculated using Fisher's exact test, values of p<0.05 were considered statistically significant. Results were expressed as % animals protected.

TABLE I

| Example | Antithrombotic activity (% protection at a dose of 90 μmol/kg, p.o.) | | | |
|---|---|---|---|---|
| | ½ h | 1 h | 2 h | 4 h |
| Comp 1 | n.d. | 50 @ 230 μmol/kg | 32 | 16 |
| Comp 2 | n.d. | 33 | n.d. | n.d. |
| Comp 3 | n.d. | 32 | n.d. | n.d. |
| Comp 4 | n.d. | 20 | 0 | 0 |
| Comp 5 | n.d. | 16 | 0 | 0 |
| Comp 6 | 40 | 16 | 0 | 0 |
| Comp 7 | 0 | 0 | 0 | 0 |
| Comp 8 | n.d. | 33 | n.d. | n.d. |
| Comp 9 | n.d. | n.d. | n.d. | n.d. |
| Comp 10 | n.d. | 40 | n.d. | n.d. |
| Comp 11 | n.d. | 32 | n.d. | n.d. |
| Comp 12 | n.d. | 40 | n.d. | n.d. |
| Ej. 1 | n.d. | 32 | n.d. | n.d. |
| Ej. 2 | n.d. | 67 | n.d. | n.d. |
| Ej. 3 | n.d. | 67 | n.d. | n.d. |
| Ej. 4 | 32 | 67 | 83 | 50 |
| Ej. 5 | 40 | 76 | 67 | 50 |
| Ej. 6 | n.d. | 67 | 34 | 17 |
| Ej. 7 | 50 | 84 | 32 | 0 |
| Ej. 8 | n.d. | 100 | 50 | 0 |
| Ej. 9 | n.d. | 83 | 50 | 0 |
| Ej. 10 | 67 | 75 | 83 | 40 |
| Ej. 11 | n.d. | 66 | n.d. | 0 |
| Ej. 12 | n.d. | 32 | n.d. | 16 |
| Ej. 13 isom 1 | n.d. | 32 | n.d. | 16 |
| Ej. 13 isom 2 | n.d. | 83 | n.d. | 16 |
| Ej. 14 isom 1 | n.d. | n.d. | n.d. | n.d. |
| Ej. 14 isom 2 | n.d. | n.d. | n.d. | n.d. |
| Ej. 15 | n.d. | 9 | n.d. | 0 |
| Ej. 16 | n.d. | 40 | n.d. | 20 |

Anti-Anginal Activity Assessment

Male Wistar rats weighing 250-300 g were used after an acclimatization period of five days, and animals were divided in groups of 8 for each treatment. In all experiments, rats were treated with 90 μmol/kg of each product by oral gavage using an administration volume of 10 ml/kg unless otherwise stated. The vehicle used to dissolve the products consisted of 1% Cremophor EL 27963, 1% Tween 80 and 0.5% Methocel E-15 in distilled water. After a fasting period of 8 h with free access to drinking water, each product was given by gavage 1 h before induction of angina.

The procedure used to test the anti-anginal activity was that described by Hirata Y et al (Hirata Y, et al. Journal of Cardiovascular Pharmacology 1998, 31: 322-326).

After treatment, animals were anaesthetized with pentobarbital and electrodes were set for standard limb lead II electrocardiogram recording (Grass polygraph model 7, amplifier 7DA and pre-amplifier 7P1).

To induce coronary angina caused by coronary obstruction, a 35%-ferric chloride embedded mini patch was applied onto the left anterior descending coronary artery just below the left auricle. In all groups, after application of the patch, the ECG was recorded during 10 minutes. The shortening of the S-wave amplitude was measured on the recorded ECG. Data were collected with a Biopac system model MP100 connected to a Pentium PC. Results were expressed as % inhibition of S-wave decrease vs the untreated control.

TABLE II

| | Antianginal activity (% inhibition of S-wave decrease at a dose of 90 μmol/kg, p.o.) | | | |
|---|---|---|---|---|
| | ½ h | 1 h | 2 h | 4 h |
| Comp 1 | 0 | 0 | 50 | n.d. |
| Comp 2 | n.d. | n.d. | n.d. | n.d. |
| Comp 3 | n.d. | n.d. | n.d. | n.d. |
| Comp 4 | n.d. | n.d. | n.d. | n.d. |
| Comp 5 | n.d. | n.d. | n.d. | n.d. |
| Comp 6 | n.d. | 48 | n.d. | 0 |
| Comp 7 | n.d. | 73 @ 450 μmol/kg | n.d. | n.d. |
| Comp 8 | n.d. | n.d. | n.d. | n.d. |
| Comp 9 | n.d. | n.d. | n.d. | n.d. |
| Comp 10 | n.d. | n.d. | n.d. | n.d. |
| Comp 11 | n.d. | n.d. | n.d. | n.d. |
| Comp 12 | n.d. | n.d. | n.d. | n.d. |
| Ej. 1 | n.d. | 29 | n.d. | 0 |
| Ej. 2 | n.d. | 69 | n.d. | 8 |
| Ej. 3 | n.d. | n.d. | n.d. | n.d. |
| Ej. 4 | n.d. | 84 | n.d. | 43 |
| Ej. 5 | n.d. | 87 | n.d. | 58 |
| Ej. 6 | n.d. | n.d. | n.d. | n.d. |
| Ej. 7 | n.d. | 81 | n.d. | 23 |
| Ej. 8 | n.d. | 77 | n.d. | 25 |
| Ej. 9 | n.d. | n.d. | n.d. | n.d. |
| Ej. 10 | n.d. | 69 | n.d. | 57 |
| Ej. 11 | n.d. | 41 | n.d. | n.d. |
| Ej. 12 | n.d. | 14 | 0 | 0 |
| Ej. 13 isom 1 | n.d. | 27 | n.d. | 5 |
| Ej. 13 isom 1 | n.d. | 98 | n.d. | 33 |
| Ej. 14 isom 1 | n.d. | n.d. | n.d. | n.d. |
| Ej. 14 isom 2 | n.d. | n.d. | n.d. | n.d. |
| Ej. 15 | n.d. | 21 | 0 | 0 |
| Ej. 16 | n.d. | 32 | n.d. | 30 |

As it may be seen from tables I and II, the compounds of the present invention posses superior antianginal and/or antithrombotic activity lasting longer than those of comparative compounds belonging to the state of the art.

The invention claimed is:

1. A compound of formula (I), or a tautomer or a pharmaceutically acceptable salt thereof:

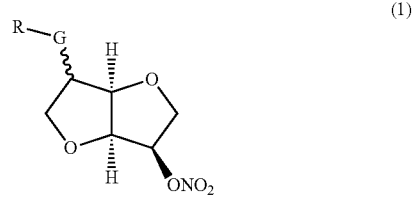

wherein G represents a —S(O)$_n$— group where n is 1; and R is ethyl.

2. A pharmaceutical composition comprising as an active ingredient at least one compound according to claim 1 together with one or more pharmacologically acceptable excipients.

3. The pharmaceutical composition according to claim 2 additionally comprising one or more additional active ingredients chosen from the group comprising thrombolytic agents, anticoagulant agents, antithrombotic agents, immunoglobulins or fragments thereof, hypolipemiant agents and antioxidant/free radical scavenging agents.

4. A pharmaceutical composition according to claim 2, wherein said at least one compound has the formula:
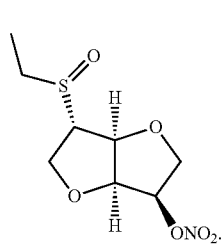
5. A compound of the formula:
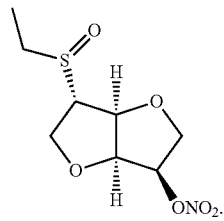
* * * * *